United States Patent [19]

Zoechbauer

[11] Patent Number: 5,218,422
[45] Date of Patent: * Jun. 8, 1993

[54] INTERFEROMETRIC ANALYZER FOR MULTIPLE SUBSTANCE DETECTION

[75] Inventor: Michael Zoechbauer, Oberursel, Fed. Rep. of Germany

[73] Assignee: Hartmann & Braun, Frankfurt, Fed. Rep. of Germany

[*] Notice: The portion of the term of this patent subsequent to Mar. 12, 2008 has been disclaimed.

[21] Appl. No.: 562,226

[22] Filed: Aug. 3, 1990

[30] Foreign Application Priority Data

Aug. 3, 1989 [DE] Fed. Rep. of Germany ....... 3925692

[51] Int. Cl.⁵ .................................................. G01B 9/02
[52] U.S. Cl. ..................................... 356/352; 356/346
[58] Field of Search ................ 356/346, 351, 352, 418

[56] References Cited

U.S. PATENT DOCUMENTS 4,090,792 5/1978 Bunge .................................. 356/418
4,999,013 3/1991 Zoechbauer ......................... 356/346

Primary Examiner—Samuel A. Turner
Attorney, Agent, or Firm—Ralf H. Siegemund

[57] ABSTRACT

An interferometric analyzer for the detection of substances having a structured absorption spectrum such as a periodic or quasiperiodic absorption line pattern, within a gas blend, and comprising a source of radiation for directing radiation into a radiation path that includes a container, cell or the like which contains the substances to be detected, the path includes further a filter system, which includes an electrically or temperature controlled Fabry Perot element such that the spacing between the transmission lines of the interference corresponds to spacing of absorption lines of different substances for different absorption bands of these substances; and a dispersion filter each circularly variable or another Fabry Perot filter is positioned in the radiation path for selecting a respective spectral region as far as a particular substance is concerned by means of the controlled disperging element.

12 Claims, 2 Drawing Sheets

INTERFEROMETRIC ANALYZER FOR MULTIPLE SUBSTANCE DETECTION

BACKGROUND OF THE INVENTION

The present invention relates to an interferometric analyzer for detecting several different substances in a blend, and more particularly the present invention relates to multiple substance, interferometric analyzers under the assumption that the substances being present in a blend have a particularly structured absorption spectrum such as a periodic or quasiperiodic spectrum, or at least a well defined band edge.

Equipment of the kind to which the invention pertains includes usually a source of radiation having and providing a radiation path in which is positioned a sample of the substance to be investigated and in which particular substances of interest are presumably included; the equipment moreover may include a selective filter and a detector which converts radiation into an electrical signal that is representative of the information sought.

German printed patent application 32 06 472 discloses a measuring device for the optical gas analysis of plural (n) different components in a blend. A particular example elaborated on is related to the detection of carbon monoxide, sulfur dioxide and water. Here one uses the method of comparing wavelengths. A rotating filter wheel with several different optical filters establishes a certain selectivity concerning particular selective wavelengths in the radiation. The time multiplexed output of the detector is processed in a computer facility which calculates the radiation extinction as far as it is contributed to by the various components.

This particular device is disadvantaged by the fact that it has only a limited optical selectivity. All other, that is parasitic and thus interfering absorption through companion gases, and depending on their respective absorption spectrum, are also and more or less indiscriminately ascertained. Thus the interference components have to be compensated in some fashion, for example calculated out of the result in an algebraic process, namely by calculating results using a system of algebraic equations. This calculation will yield exact results only if one assumes the validity and applicability without limitation of the Lambert-Beer absorption law. That is sometimes more or less the case but sometimes it is not. Problems result when the companion gas concentration varies to a considerable degree so that in fact now deviations from the Lambert-Beer law do occur.

The German printed patent application 36 25 490 describes a multicomponent process analyzer system which uses a disperging optic in form of a grating grid monochromatic analyzer for spectrum analysis and separation. Here a particular use is made of an imaging element realized by a slit. Inherently, then this device is of low intensity and marginal yield. Moreover for compensation and eliminating the effect of interfering companion gas in the absorption, it is also here necessary to solve a more or less complex equation system.

Still another device for determining several components in an exhaust gas blend is described in German printed application 25 59 806. The device uses also here a filter wheel for spectral separation of various components with follow-up and supplemental calculation to obtain corrections. The disadvantages outlined above are also applicable because they refer to this kind of system in principle, irrespective of construction details.

Another multicomponent analyzer is known for example through the company ELF AQUITAINE described in a prospectus called "Gas analyzer using Optical Interferometry" published by that company - L Cdex Paris. The device is provided here for the detection of several substances under utilization of a characteristic optical path difference, and the device employed includes the following elements. There is a Wollaston prism used as a polarizer then there is a photoelectric modulator, a birefringent plate element having a thickness that corresponds to the characteristic path difference of the substances; next is provided a second Wollaston prism as an analyzer; and finally, there is a disperging element which is a holographic grid with several associated output slits and detector elements.

It was found that for gas analyses in the infrared region and for simultaneously detecting carbon monoxide, nitrogen monoxide and sulfur dioxide there is no adequate material available that does have the requisite birefringent characteristics, with an adequate degree of transmissivity; so that this device no matter what its value is not applicable for measuring the detection of these particular gas components.

DESCRIPTION OF THE INVENTION

It is an object of the present invention to provide a new and improved gas analyzer that includes a source of radiation, a container or the like for the sample gas to be investigated, a controllable filter and a detector.

It is a more general object of the present invention to provide a new and improved analyzer for the individual detection of different substances each assumed to have structured, such as periodic or quasiperiodic absorption structure.

It is another object of the present invention to provide a new and improved analyzer which enables the detection of molecules with an absorption structure that is periodic or quasiperiodic spectrum, and in a highly selective fashion avoiding the drawbacks outlined above.

In accordance with the preferred embodiment of the present invention it is suggested to use a single controlled Fabry Perot interference filter element having a thickness such that the resulting distance or spacing of the interference line corresponds to the spacing of absorption lines of several substances within the chosen spectrum range and that the selection of the respective substance to be detected in that range is used under utilization of a dispersion filter.

The invention is inter alia based on the discovery and recognition of the interesting phenomenon that different substances though having different absorption bands often have similar absorption band spacings. Hence, one and the same interference filter of the Fabry Perot type has a transmitting line pattern that covers, on the average, all these bands and line spacings, and a versatile front end disperging filter just limits the detection to the different bands as pertaining to the different substances, and one band after another is used by the interference filter to detect the respective different substances. The detector process proper in each instance (i.e. for each substance) may include, placing the transmission lines of the interference filter to match the absorption lines of the particular substance as per a particular band, and alternatingly shifting the transmission lines by e.g. one-half spacing, i.e. in between the absorption line patterns.

The difference is detected output which is indicative of that substance. The process is repeated for different bands i.e. for the detection of the other substances.

The process being employed specifically in the detection depends to some extent on the relative width of transmission and absorption lines. The preferred method is to alternate between a complete match and a complete nonmatch between the absorption line spectrum and the pattern of transmission lines of the interference plate, as described in the preceding paragraph. A second method uses a single transmission line assumed to be very narrow as compared with the spacing between absorption lines and also uses the match/mismatch principle by a controlled shifting of the frequency of the transmission line. The third method relies on a structure of the (relatively wide) absorption line but having a steep (high gradient) edge portion; and the transmission line of the filter is moved across that edge. In each case, of course, there is another filter that limits the radiation to that particular band portion which includes the structured and used absorption lines of any substance to the exclusion of other substances!.

The interferometric analyzer in accordance with the invention provides the detection of multiple substances with periodic and quasiperiodic or otherwise structured by any spectrum using electrical or a thermally tunable Fabry Perot interference element, as they are described and used in my patent applications Ser. No. 388,723, filed Apr. 14, 1989 and German application P3923831 corresponding to U.S. application, Ser. No. 551,419, filed Jul. 12, 1990.

In one case, the filter element has its interference line spacing and positioning controlled electrically; in the other one thermally. The two cases describe different kinds of detection methods; they are all applicable here and are incorporated by reference accordingly.

The thickness of the filter element in either case is selected and controlled so that the distance of the resulting interference lines corresponds to the distance in absorption line of the substance to be detected. As stated, the interference element is either an electrooptically controlled or is of the thermooptically controlled kind or it is a cell which is filled with liquid crystal of a double refractory (birefringent) variety that is also electrically controlled. The modulation is carried out by applying a voltage to the semitransparent and reflective front sides of the plate or the cell, or, depending on the variety chosen, by changing its temperature. The interferometric analyzer thus uses the fact that certain molecules have almost identical spacing between their absorption line within a certain periodic band showing a periodic repetition of absorption line.

The phenomenon is used e.g. for the infrared range in carbon monoxide, nitrogen monoxide and sulphur dioxide. Here one should, for example, consider the vibration/rotation bands of the molecules in the 2144 cm$^{-1}$ band, the 1887 cm$^{-1}$ band and the 1151 cm$^{-1}$ band respectively for the three substances. The band center in each instance exhibits line spacings of 3.8 cm$^{-1}$ for CO; of 3.5 cm$^{-1}$ for NO and 4.0 cm$^{-1}$ for SO$_2$. Owing to the unharmonicity of the rotational spectral line, within a vibration rotation band, they are not exactly equidistantly spaced but the spacing declines with increasing wave number. Thus, for many kinds of molecules one can in fact find a particular wave number range such that the spacing of the rotational absorption lines really is the same or almost the same for all (three) different kinds of molecules. This means that for the selective simultaneous detection of these molecules one needs in fact only one tunable element. As stated, for obtaining a differentiation among the various kinds of molecules it is necessary to use suitable front end filter to limit the spectral range to that particular portion that is of interest and coverable by the controlled interference filter. That selection can be carried out by means of a circularly (azimuthally) variable, sectorlike filter, or by another Fabry-Perot element, controlled so that its lines are relatively broad and cover (possibly also by way of shifting) the particular absorption bands of all the substances.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 illustrates a relatively broad band spectrum light source L emitting light into illustrated horizontally appearing light and radiation transmission path. There is a rotational circularly variable band filter F that limits the rather broad spectrum to different limited ranges, in toto covering the range that is being used for the analysis by operation of the various elements to be described shortly. In the case of CO, NO and SO$_2$ detection, the filter F has sectors covering relatively narrow transmission bands around 2144 cm$^{-1}$ (CO), 1887 cm$^{-1}$ (NO) and 1151 cm$^{-1}$ (SO$_2$). "Narrow" means in relation to the entire IR band, but of course each filter sector covers for transmission a frequency range that includes many absorption lines for the respective substances within the respective band.

Figure 1:
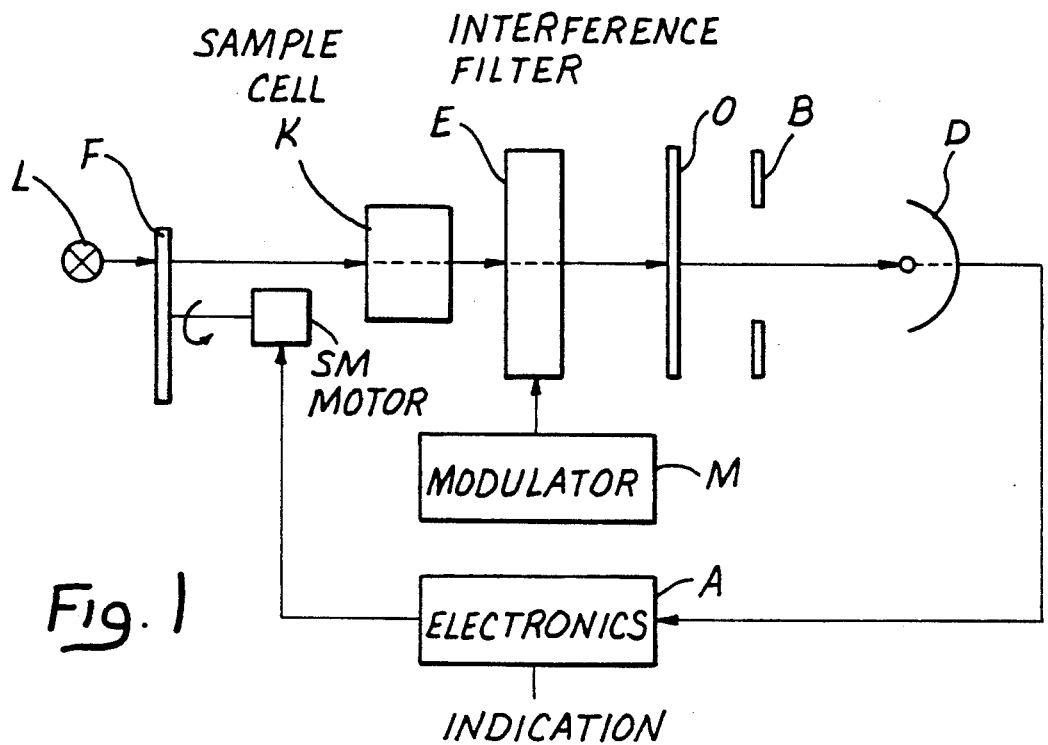
FIG. 1 is a schematic block diagram of an example for the preferred embodiment of practicing the best mode considerations.

Step motor SM drives this particular filter disk F to put one sector after the other into the light path. An electronic circuit A controls the motor SM such that the placement of various components (filter sectors concerning) the spectral ranges of interest can be tracked. In other words the equipment "knows" which particular portion and sector of the filter F has been positioned into the light path by the operation of the step or position trackable motor SM and thereby provides the requisite information concerning the particular kind of filter action then provided.

Downstream from the filter F is provided a container, a cuvette, a flask K, etc. containing a sample of the gas to be investigated. Of course the flask itself is made of material that is adequately transparent to the radiation passing through. There is no basic limitation intended here with regard to this particular device. It may also be a transparent portion of a chimney, an exhaust pipe or the like.

Downstream from the sample cell K is provided a tunable Fabry Perot element E. This is either an electro-optically controlled plate or it is a thermooptically controlled plate or it is an electrically controlled cell filled with liquid crystals. Different examples of this kind are shown and will be described below with reference to FIGS. 2, 3, 4 respectively. A modulation unit M provides the requisite control for the Fabry Perot element in order to shift and position and space the interference lines produced by that unit. Depending on the kind of element E the control is either directly an electrical one for providing electro-optical control as is for example described in copending application Ser. No. 388,723, filed Apr. 14, 1989, corresponding to German printed application P3812334. In the alternative the element E may be provided for thermooptical control as is shown for example in the copending application Ser. No. 551,419 corresponding to German application B3923831.

These two copending applications describe several modes of operation which are adopted and applicable also here: for particular signal that is applied to the filter E, it sets up a pattern of transmission lines (separated by relative opaqueness) in relation to frequency. A change in applied signal moves that pattern, for example to place the transmission lines now where previously there was an opaque portion. By having in one instance the absorption lines of a substance coincide with the transmission lines, in the other instant not, a pattern of overall transmission or transmissivity is generated that maximizes on the selectivity towards a particular substance that has those absorption lines (to be exclusive of other substances).

Downstream from the tunable fabry perot element E is positioned an objective O following which is provided a diaphragm B to limit the range to be subjected to interferometric evaluation to a central, that means optical axis near range or zone. The radiation permitted to pass by a diaphragm B is detected by means of an electrooptical detector D which converts the radiation it receives into an electrical signal. The signal is fed to the processing unit A which is an electronic circuit providing further evaluation and providing also a synchronization control for the motor SM. Basically electronic circuit A produces an output switch will represent the concentration of the various components to be detected.

The various components are of course distinguished by the selection made by filter F, to limit the radiation that actually passes through elements K,E, etc. narrowly to a band characteristic of a substance. Hence, for the detection of CO, filter F limits the radiation to the 2144 band so that the filter E can superimpose its transmission line pattern upon the light band that was filled out by F and that has been selectively absorbed by any CO in container K. Next, filter F with pass the 1887 band for NO detection and filter E will superimpose basically the same pattern upon that radiation, following using the 1151 band for SO2 detection in the same fashion.

Figure 2:
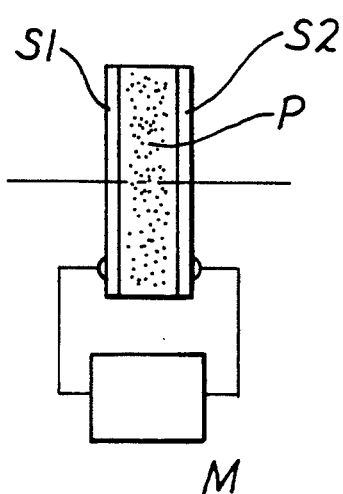
FIG. 2 is a cross section through a tunable Fabry Perot element of the electrical control variety.
Figure 3:
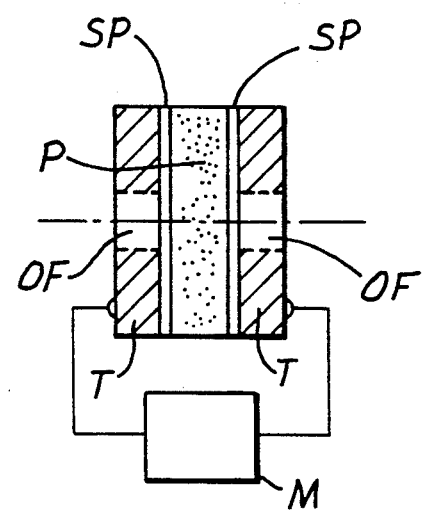
FIG. 3 is a different Fabry Perot element of the kind used for temperature control of the transmission.
Figure 4:
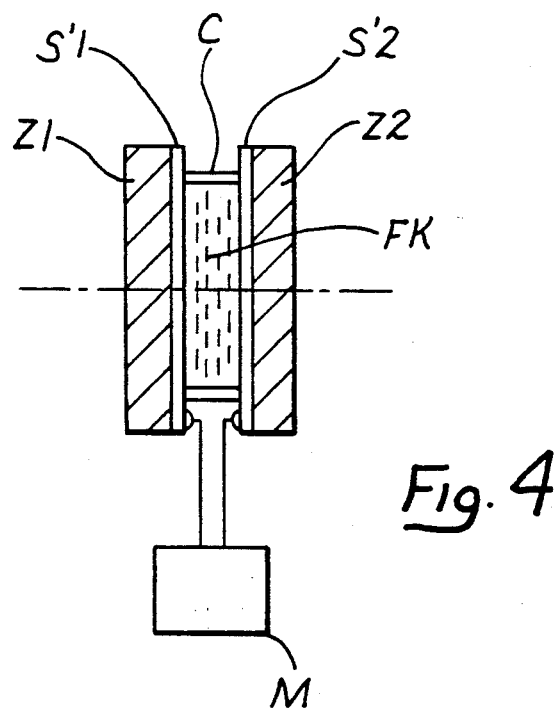
FIG. 4 is a liquid crystal cell that can be used in the example shown in FIG. 1.

FIGS. 2-4 illustrate various examples for the Fabry-Perot element E and the process as it is carried out in the operation and as it functions in each instance will now be described with reference to these different versions for the Fabry-Perot filter element E. In FIG. 2 is illustrated an electrooptical sample corresponding to the kind disclosed in application Ser. No. 388,723 of Apr. 14, 1989 by me and another. The filter element E is comprised of a thin plate P made of electrooptical material such as lithium niobate carrying semitransparent, semireflective electrode layers S1 and S2. These electrodes to the extent their function is that of semitransparent mirrors, are selected to adjust the degree of reflection and in accordance with the desired half value width of the interference line. The electrodes S1 and S2 are connected electrically to the modulation unit M which in this case is simply provided with voltage to be effective between the electrodes S1 and S2. That voltage varies the degree of transmissivity of the plate P in that in it shifts and positions the interference lines of this filter.

FIG. 3 illustrates the element E but being in this case constructed as a thermooptical unit of the kind disclosed in my copending application Ser. No. 551,419. This plate P is made of a material having as large as possible a temperature dependence on the optically effective product of plate thickness and index of refraction. A suitable material is either silicon or zinc selenide. For adjusting the temperature of the plate P Peltier elements T are provided which have small gap or openings OF in the center for unrestrictive passage of light through these openings OF while covering the major part of the plate to control the temperature thereof. The control of heating or cooling is carried out through the modulation unit M providing an electrical signal since the Peltier elements are such that convert electricity into temperature differentials. For reducing the half value width of the interference lines of that filter again semitransparent mirrors SP are provided, on the flat side of the plate P, and in that regard they function similar to the layers SP and SP but they do not function as electrodes in this case.

FIG. 4 finally shows a Fabry Perot element E constructed as a liquid crystal cell. The cell is basically a container with windows Z1 and Z2 being provided on the inside with transparent electrodes S'1 and S'2. A spacer C defines the thickness of the cell i.e. the distance between the two cell windows Z1 and Z2. The cell is filled with liquid crystal material FK of a known variety. The modulation unit M has its electrical output connected to the electrodes S'1 and S'2 and provides the control voltage to shift the transmission characteristics of the Fabry Perot element E. The electrodes S1 and S2 in this case may also be constructed as semitransparent mirrors in order to adjust the half values width of the interference lines.

Figure 5:
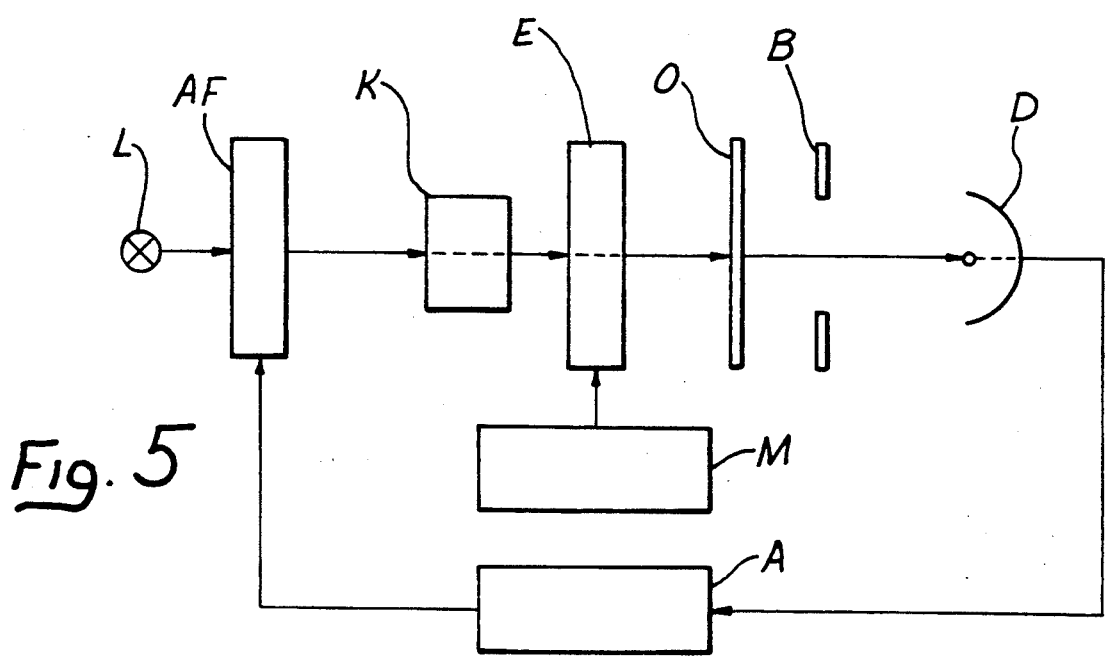
FIG. 5 illustrates a modification of the diagram shown in FIG. 1 to be explained in greater detail below.

In lieu of the filter F as a section circularly variable filter one could use a broad band Fabry Perot filter AF which is shown by way of example in FIG. 5. The other elements O,B,D,L are the same as in FIG. 1 and in principle the electronics A is similar, but the input filter directly downstream from the light source is in this case provided as a Fabry Perot element. Preferably for reasons of obtaining disperging function one uses liquid crystal cell of the kind shown in FIG. 4. The cell thickness of this tunable filter is to be selected so that an interference pattern obtains with as large as possible between the interference lines. This is the result of selecting the cell thickness of Fabry-Perot filter AF to adjust a few micrometers. The control of the filter is carried out through the electronics such that the individual measuring components will be produced for ascertaining within the spectral region of interest.

The invention is not limited to the embodiments described above but all changes and modifications thereof, not constituting departures from the spirit and scope of the invention, are intended to be included.

I claim:

1. Interferometric analyzer for the detection of substances having a structured absorption spectrum such as a periodic or quasiperiodic absorption line pattern, within a gas blend, and comprising a source of radiation for directing radiation into a radiation path that includes a container, cell or the like which contains the substances to be detected, the path further including a Fabry Perot element the thickness of which is determinative for the transmission interference lines, and a detector downstream from the Fabry Perot element, the improvement comprising:

means for controlling the thickness of the Fabry Perot element such that the spacing between the transmission lines of the interference corresponds to spacing of absorption line of different substances for different absorption bands of these substances; and a disperging element positioned in the radiation path for selecting a respective spectral region as far as a particular substance is concerned by means of the controlled disperging element.

2. Interferometric analyzer as in claim 1, the Fabry Perot element being an electrooptical plate carrying semitransparent, semireflective electrodes.

3. Interferometric analyzer as in claim 1, said Fabry Perot element being a cell filled with a liquid crystal, front and rear windows of the element being provided with semitransparent electrodes.

4. Interferometric analyzer as in claim 1, said Fabry Perot element being a thermooptically active plate carrying semitransparent surfaces, there being means for controlling the temperature of said plate.

5. Interferometric analyzer as in claim 1, said disperging element being a rotating variable filter.

6. Interferometric analyzer as in claim 1, said disperging element being a broad band tunable Fabry Perot element.

7. Interferometric analyzer for the detection of multiple substances which includes filter means, a source of radiation, a cell for containing substances and being passed through by radiation from the source, and a detector for detecting radiation permitted to pass the filter means and the cell, the improvement of the filter means comprising, a first controllable interference filter having shiftable narrow transmission lines together covering a relative broad spectrum including at least an absorption band per substance to be detected; and a second filter for selecting different bands for different substances, one after the other, for selective detection of the substances by means of operation of the controllable interference filter.

8. Analyzer as in claim 7, the interference filter being a Fabry Perot element.

9. Interferometric analyzer as in claim 8, the Fabry Perot element being an electrooptical plate carrying semitransparent, semireflective electrodes.

10. Interferometric analyzer as in claim 8, said Fabry Perot element being a cell filled with a liquid crystal, front and rear windows of the element being provided with semitransparent electrodes.

11. Interferometric analyzer as in claim 8, said Fabry Perot element being a thermooptically active plate carrying semitransparent surfaces, there being means for controlling the temperature of said plate.

12. Interferometric analyzer as in claim 8, said second filter being a broad band tunable Fabry Perot element.

* * * * *